United States Patent [19]

McCurry, Jr. et al.

[11] Patent Number: 5,266,690
[45] Date of Patent: Nov. 30, 1993

[54] PREPARATION OF ALKYLPOLYGLYCOSIDES

[75] Inventors: Patrick M. McCurry, Jr., Lansdale; Robert S. McDaniel, Chalfont; William G. Kozak, Hatfield; Allen D. Urfer, Lansdale, all of Pa.; Gail Howell, Fort Mill, S.C.

[73] Assignee: Henkel Corporation, Ambler, Pa.

[21] Appl. No.: 810,588

[22] Filed: Dec. 19, 1991
(Under 37 CFR 1.47)

[51] Int. Cl.$^5$ .............. C07H 1/06; C07H 15/04; C07H 15/00; C07G 3/00; C08B 37/00
[52] U.S. Cl. ............... 536/18.6; 536/124; 536/126; 536/127; 424/70; 252/174.17; 252/DIG. 5; 252/DIG. 13; 252/DIG. 14
[58] Field of Search ............... 536/18.6, 124, 126, 536/127; 424/70; 252/174.17, DIG. 5, DIG. 13, DIG. 14; 514/846, 881

[56] References Cited

U.S. PATENT DOCUMENTS

| | | | |
|---|---|---|---|
| 2,390,507 | 12/1945 | Cantor | 536/18.6 |
| 3,219,656 | 11/1965 | Boettner | 260/210 |
| 3,547,828 | 12/1970 | Mansfield et al. | 252/351 |
| 3,598,865 | 8/1971 | Lew | 260/210 |
| 3,707,535 | 12/1972 | Lew | 260/210 |
| 3,772,269 | 11/1973 | Lew | 260/210 |
| 3,839,318 | 10/1974 | Mansfield | 260/210 |
| 4,154,706 | 5/1979 | Kenkare et al. | 252/547 |
| 4,196,201 | 4/1980 | Boelle et al. | 424/180 |
| 4,304,679 | 12/1981 | Hooper et al. | 252/106 |
| 4,323,468 | 4/1982 | Grollier et al. | 252/174.17 |
| 4,349,669 | 9/1982 | Klahr et al. | 536/127 |
| 4,393,203 | 7/1983 | Mao et al. | 536/124 |
| 4,396,520 | 8/1983 | Payne et al. | 252/89.1 |
| 4,472,170 | 9/1984 | Hellyer | 44/51 |
| 4,483,779 | 11/1984 | Llenado et al. | 252/135 |
| 4,483,979 | 11/1984 | Mao | 536/18.6 |
| 4,488,981 | 12/1984 | Urfer et al. | 536/18.6 |
| 4,493,773 | 1/1985 | Cook et al. | 252/8.8 |
| 4,510,306 | 4/1985 | Langdon | 536/127 |
| 4,536,319 | 8/1985 | Payne | 252/174.17 |
| 4,565,647 | 1/1986 | Llenado | 252/354 |
| 4,597,770 | 7/1986 | Forand et al. | 44/51 |
| 4,599,188 | 7/1986 | Llenado | 252/174.17 |
| 4,606,850 | 8/1986 | Malik | 252/528 |
| 4,627,931 | 12/1986 | Malik | 252/153 |
| 4,657,999 | 4/1987 | Hoefer et al. | 526/200 |
| 4,663,069 | 5/1987 | Llenado | 252/117 |
| 4,668,422 | 5/1987 | Malik et al. | 252/174.17 |
| 4,678,595 | 7/1987 | Malik et al. | 252/174.17 |

(List continued on next page.)

FOREIGN PATENT DOCUMENTS

| | | |
|---|---|---|
| 0092355 | 10/1983 | European Pat. Off. |
| 0096917 | 12/1983 | European Pat. Off. |
| 0132043 | 1/1985 | European Pat. Off. |
| 3932173 | 4/1991 | Fed. Rep. of Germany |
| 40-7886 | 4/1965 | Japan |
| 62-99390 | 5/1987 | Japan |
| 63-288821 | 11/1988 | Japan |
| 103202 | 4/1990 | Japan |

OTHER PUBLICATIONS

"Preparation and Properties of Pure Alkyl Glucosides, Maltosides and Maltotriosides", JAOCS, vol. 61, No. 10, pp. 1651–1655, Oct. 1984.

"Physical and Functional Properties of Some Higher Alkyl Polyglucosides", JAOCS, vol. 47, pp. 162–167, 1970.

Primary Examiner—Ronald W. Griffin
Attorney, Agent, or Firm—Ernest J. Szoke; Wayne C. Jaeschke; Patrick J. Span

[57] ABSTRACT

A process for preparing high detergency or surfactant alkyl polyglycoside compositions and a purified alkyl monoglycoside and to compositions employing the polyglycosides for various end use applications. The process involves removal of a substantial portion of the monoglycoside present in a reaction product mixture containing alkyl polyglycosides resulting from the reaction of an alcohol and saccharide at elevated temperatures in the presence of an acid catalyst. Separation of the monoglycoside from the reaction product mixture may be carried out by molecular distillation.

46 Claims, 2 Drawing Sheets

U.S. PATENT DOCUMENTS

| | | | |
|---|---|---|---|
| 4,704,453 | 11/1987 | Lorenz et al. | 536/18.6 |
| 4,705,665 | 11/1987 | Malik | 422/12 |
| 4,713,447 | 12/1987 | Letton | 536/18.6 |
| 4,732,696 | 3/1988 | Urfer | 252/174.17 |
| 4,732,704 | 3/1988 | Biermann et al. | 252/548 |
| 4,748,158 | 5/1988 | Biermann et al. | 514/25 |
| 4,767,559 | 8/1988 | Kruse et al. | 252/106 |
| 4,780,234 | 10/1988 | Malik et al. | 252/135 |
| 4,820,814 | 4/1989 | Lueders | 536/18.6 |
| 4,889,925 | 12/1989 | Schmid et al. | 536/18.6 |
| 4,923,976 | 5/1990 | Arnaudis | 536/18.6 |
| 4,987,225 | 1/1991 | Pickens | 536/124 |
| 4,990,605 | 2/1991 | Lueders | 536/18.6 |
| 5,079,350 | 1/1992 | Fujita et al. | 536/18.6 |
| 5,104,981 | 4/1992 | Yamamuro et al. | 536/18.6 |
| 5,120,563 | 6/1992 | Mohlenkamp et al. | 536/1.1 |
| 5,130,420 | 7/1992 | Yamamuro et al. | 536/18.6 |

PREPARATION OF ALKYLPOLYGLYCOSIDES

BACKGROUND OF THE INVENTION

1. Field of the Invention

This invention relates to a process for preparing high-detergency alkyl polyglycoside compositions and a purified alkyl monoglycoside and to compositions employing the alkyl polyglycosides for various end-use applications. In particular, the invention, involves removal or separation of a substantial portion of the alkyl monoglycoside present in a reaction product mixture containing alkyl polyglycosides resulting from the reaction of an alcohol and a saccharide at elevated temperatures in the presence of an acid catalyst.

2. Statement of Related Art

The reaction of a reducing saccharide, e.g. an aldose or ketose saccharide, or a source thereof, with an alcohol results in the formation of a glycoside. Acids catalyze the reaction between a reducing saccharide and an alcohol. When the alcohol is an alkanol, the resulting glycoside is commonly referred to as an alkyl glycoside. Alkyl glycosides are structurally stable to alkali. Long chain, higher, alkyl ($C_{8-18}$) groups contribute to surface activity, e.g. detergency, of the glycoside. Thus, long chain alkyl monoglycosides and mixtures thereof with long chain alkyl polyglycosides are known materials, are known to be surface active in character and are known to be useful in a wide variety of household and industrial applications. It is also known that glycoside surfactants can be prepared by reacting a long chain alcohol with a saccharide reactant (e.g., a monosaccharide or a material hydrolyzable to a monosaccharide) at an elevated temperature in the presence of an acid catalyst. U.S. Pat. 4,987,225 contains an extensive listing of processes for preparing alkyl glycoside compositions. As disclosed therein, processes for preparing alkyl glycoside compositions are disclosed in U.S. Pat. No. 3,219,656 to Boettner (issued Nov. 23, 1965); U.S. Pat. No. 3,547,828 to Mansfield et al. (issued Dec. 15, 1970); U.S. Pat. No. 3,598,865 to Lew (issued Aug. 10, 1971); U.S. Pat. No. 3,707,535 to Lew (issued Dec. 26, 1972); U.S. Pat. No. 3,772,269 to Lew (issued Nov. 13, 1973); U.S. Pat. No. 3,839,318 to Mansfield (issued Oct. 1, 1974); U.S. Pat. No. 4,349,669 to Klahr (issued Sep. 14, 1982); U.S. Pat. No. 4,393,203 to Mao et al. (issued Jul. 12, 1983); U.S. Pat. No. 4,472,170 to Hellyer (issued Sep. 18, 1984); U.S. Pat. No. 4,483,979 to Mao (issued Nov. 20, 1984); U.S. Pat. No. 4,510,306 to Langdon (issued Apr. 9, 1985); U.S. Pat. No. 4,597,770 to Forand et al. (issued Jul. 1, 1986); U.S. Pat. No. 4,704,453 to Lorenz et al. (issued Nov. 3, 1987); U.S. Pat. No. 4,713,447 to Letton (issued Dec. 15, 1987); published European Application No. 83302002.7 (EPO Publication No. 0092355; Vander Burgh et al; published Oct. 26, 1983); published European Application No. 83200771.0 (EPO Publication No. 0096917; Farris; published Dec. 28, 1983); and published European Application No. 84303874.6 (EPO Publication 0132043; published Jan. 23, 1985).

During the course of the aforementioned acid-catalyzed saccharide reactant/long chain alcohol reaction process there is usually employed a substantial stoichiometric excess of the long chain alcohol reactant. The resulting reaction product mixture as initially made (i.e., without any intervening separation, fractionation or purification operations) typically contains a substantial molar excess of residual unreacted long chain alcohol, the monoglycoside of the long chain alcohol as the predominant glycoside molecular species both a mole and weight percentage bases, and the various higher degree of polymerization long chain alcohol polyglycoside species in progressively decreasing percentage amounts or proportions.

In accordance with the various prior art references, it has been conventional practice to remove the residual unreacted long chain alcohol from the indicated reaction mixture via various techniques such as vacuum distillation, organic solvent (e.g. acetone) extraction or fractionation, and thin (or wiped) film evaporation.

Several methods of removal of the alcohols from the crude alkyl polyglycoside reaction product have been proposed. In Japanese Application No. 63-256398, laid open Apr. 16, 1990, No. 02-103202, a method of removing the alcohol by supercritical gas extraction, more specifically carbon dioxide, is described. In German Application DE 3932173, a two-stage distillation separation of alcohol from the mixture of alkyl glycosides is described using a falling film evaporator and thin film evaporator. Another distillation separation of alkyl glycosides and alcohol is described in U.S. Pat. No. 4,889,925 in which a viscosity-reducing agent is added to the alcohol-glycoside reaction mixture, which is then distilled at a temperature up to about 160° C. at a pressure of about 1 to $10^{-3}$ mbar.

If the long chain (fatty) alcohol is removed from the reaction mixture by one of the distillation or evaporation methods, the polysaccharide by-products and any other materials with low volatility remain in the alkyl glycoside product. Thus, in each of the methods described above the intent is to remove the alcohol leaving behind the alkyl glycosides, including the alkyl monoglycoside. The product will contain the monoglycoside of the long chain alcohol as the predominant glycoside species on a percentage basis and various higher degree of polymerization long chain alcohol polyglycoside species in progressively decreasing mole percentage amounts or proportions from the DP2 through DP10 and higher glycosides.

Applications or Use Background

Since the practice of commercial scale processes for the production of alkyl polyglycoside products is governed chiefly by economic factors, it is not economically feasible to produce a wide variety of alkyl polyglycoside products for distribution in commerce. This is unfortunate since the applications or end use of these compositions is highly dependent on combinations of factors including carbon chain length, degree of polymerization, and additional factors such as the co-presence of impurities or minor amounts of residual surfactants. A wide variety of applications of alkyl polyglycoside products is known in the prior art. Illustrations of such uses include hard surface cleaner compositions, U.S. Pat. Nos. 4,606,850, 4,627,931; polymerizations acids, U.S. Pat. No. 4,657,999; liquid soaps and bubble baths, U.S. Pat. No. 4,668,422; carpet shampoo and cleaning uses, U.S. Pat. No. 4,678,595; corrosion inhibitors, U.S. Pat. No. 4,705,665; dishwashing detergents, U.S. Pat. No. 4,732,704; viscosity modifiers, U.S. Pat. No. 4,732,696; potentiating agents, U.S. Pat. No. 4,748,158; contact lens cleaning, U.S. Pat. No. 4,767,559; detergent and shampoos, U.S. Pat. Nos. 4,780,234, 4,565,647, 4,663,069, 4,483,779, 4,396,520, 4,599,188, 4,493,773, 4,536,319, 4,154,706, 4,304,679;

and cosmetics, 4,323,468, 4,196,201. This list is not intended to be all inclusive but merely to illustrate the wide variety of applications and end uses of alkyl polyglycoside compositions requiring specialized formulation considerations, which for the most part must be determined empirically.

Donald E. Koeltzow and Allen D. Urfer, in a paper, "Preparation and Properties of Pure Alkyl Glucosides, Maltosides and Maltotriosides", JAOCS, Vol. 61, No. 10, pp. 1651-1655, October, 1984, examines various physical and functional properties of relatively pure alkyl glycosides having from 4 to 18 carbon atoms. This paper in turn refers to other publications dealing with synthesis of alkyl glucosides and an article by Francis A. Hughes and Baak W. Lew, reports on the physical and functional properties which render them suitable for use on biodegradable, surfactants, emulsifiers and detergents, "Physical and Functional Properties of Some Higher Alkyl Polyglucosides", JAOCS, Vol. 47, pp. 162-167, 1970.

While these mixtures of monoglycosides and higher polyglycosides have properties permitting their function as detergents and surfactants, they have been typically formulated in the past with other anionic, nonionic or cationic surfactants to provide for enhanced surfactant properties, since standing alone they fell short of properties achieved by other surfactants, such as the ethoxylated surfactants.

SUMMARY OF THE INVENTION

It has now been discovered that an alkyl polyglycoside product having improved properties, particularly detergent or surfactant properties may be provided by removing a substantial portion of the alkyl monoglycoside (as will be described in more detail hereinafter). By removal of the portion of alkyl monoglycoside as described by the method of the present invention, the distribution of the alkyl polyglycosides present in the mixture is changed which results in improved performance. Thus, the method of the present invention provides a means for changing the distribution of the polyglycoside fractions in the alkyl polyglycoside product resulting in improved properties. As indicated earlier, end-use applications are dependent not only on carbon chain length but also on degree of polymerization. The present invention provides a means for adjusting the average degree of polymerization, thus controlling the hydrophilic portion of the alkyl polyglycoside molecule to provide optimum or maximum hydrophilic-lipophilic balance (HLB) for the particular end-use application under consideration. There can, accordingly, be provided alkyl polyglycoside products having maximum stand-alone surfactant properties, thus requiring minimal, if any, formulations with other surfactants, as typically required in the past.

The present invention also results in providing a purified alkyl monoglycoside product (the removed monoglycoside) which may be employed in applications where monoglycosides find utility or for conversion to other derivatives. Thus, the present invention unexpectedly provides a two-fold benefit, (a) an improved alkyl polyglycoside product and (b) a purified alkyl monoglycoside product.

In addition, in removing the monoglycoside, residual alcohol which may remain in small amounts in the product after the removal of alcohol following completion of the reaction, is further removed along with the removed monoglycoside. Such alcohol may then be further processed to remove it from the monoglycoside and then recycled to the reaction stage, thereby providing a further economic benefit.

The foregoing is a brief summary of the present invention and advantages thereof, which will be presented and illustrated in more detail below.

DETAILED DESCRIPTION OF THE INVENTION

Other than in the operating examples, or where otherwise indicated, all numbers expressing quantities of ingredients or reaction conditions used herein are to be understood as modified in all instances by the term "about".

It is an object of this invention to provide alkyl polyglycoside compositions having a combination of physical and functional properties desired for use in a wide variety of end uses, including cosmetic, personal care and cleaning applications. It is a further, more specific object, to enable the preparation of alkyl polyglycoside compositions having maximum stand-alone surfactant properties for specific end-use applications resulting from control of the average degree of polymerization and thereby the HLB of the composition.

It is also a further object to provide a concentrated, substantially pure alkyl monoglycoside composition, essentially free of alkyl polyglycoside fractions, by separating the alkyl monoglycoside fraction from the mixture of mono and polyglycosides resulting from the reaction of an alcohol having from about 6 to about 20 carbon atoms and a saccharide in the presence of an acid catalyst.

Figure 2A:
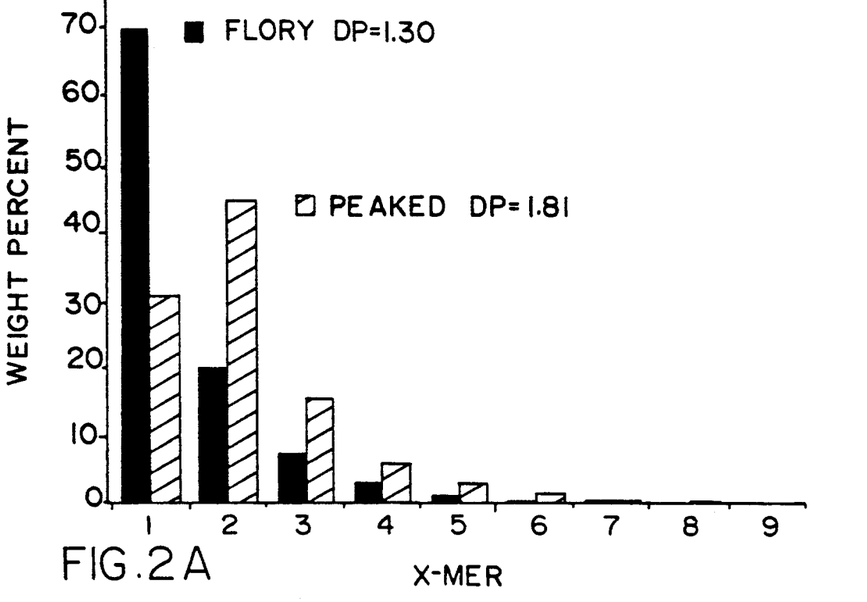
FIGS. 2A and 2B are bar graph representations of the reaction product before the use of the present invention and after use of the present invention. The solid bars show a typical Flory distribution of oligomer (x-mer) fractions in the reaction product having an average Flory DP in FIG. 2A of 1.3 and an average Flory DP in FIG. 2B of 1.70. The hatched bars show a "peaked" distribution after practice of the present invention having an average peaked DP of 1.81 in FIG. 2A and an average peaked DP of 2.14 in FIG. 2B, after removal of about 80%. and 60% of the monoglycoside respectively in FIGS. 2A and 2B.
Figure 2B:
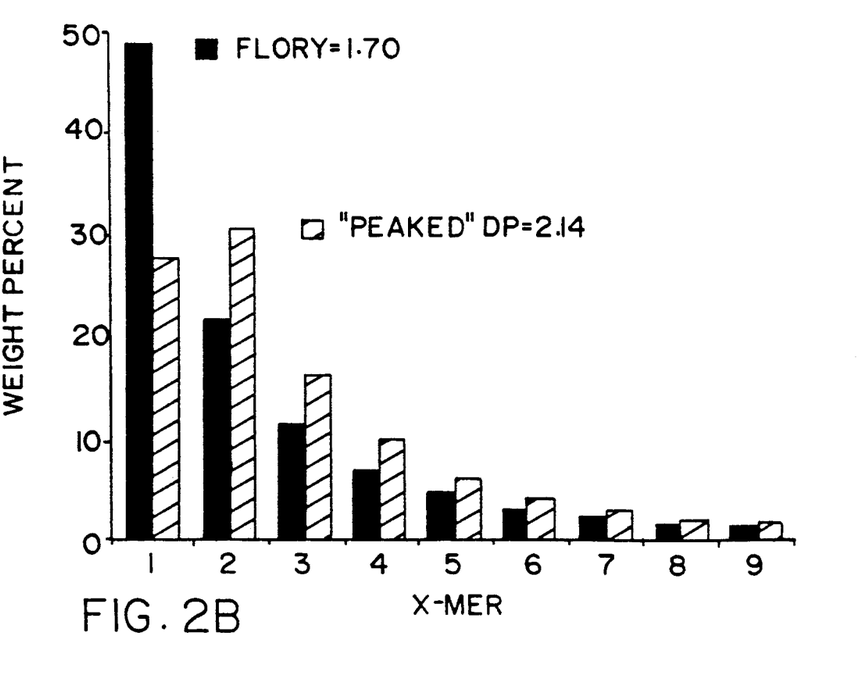

As described in the related art section above, the initial reaction product of the alcohol and saccharide in the presence of an acid catalyst results in a mixture of a monoglycoside of the alcohol and various higher degrees of polymerization (DP) polyglycosides in progressively decreasing amounts, i.e., the diglycoside (DP2), the triglycoside (DP3) and the higher polyglycosides (DP4 and higher). A typical distribution of the various oligomers provided is a Flory distribution, examples of which are seen in the solid bars of FIGS. 2A and 2B. While the specific distribution of the various fractions may vary somewhat for various reaction products, the overall distribution curve seen in the solid bars in FIGS. 2A and 2B is the same, though the average DP of the reaction mixture may vary due to the differing distribution of the various fractions, i.e., DP1, DP2, DP3 and higher fractions. Typically, the Flory distribution of the reaction product after removal of the excess alcohol will have an average degree of polymerization above 1.2, i.e., about 1.4, with a monoglycoside content in the range of about 50–70% by weight of the glycoside product. Commercially available products typically have an average Flory DP of about 1.3–1.7.

As indicated earlier by use of the method of the present invention, the distribution of the alkyl polyglycosides present in the mixture is changed resulting in a product having a peak at the DP2 and the average DP of the resulting product is higher than the average DP of the initial reaction product before removal of a portion of the monoglycoside, preferably at least about 0.2 units higher. In the past, attempts to provide an increased average DP involved control of the amounts of alcohol and saccharide and the reaction conditions, particularly temperature and time, and the nature and amount of catalyst. Rather than increasing the DP2 oligomer, such attempts resulted in either increased amounts of the higher DP oligomers, which do not result in improved surfactant or detergent properties, or resulted in increased degradation products or undesirable by-products. By means of the present invention, a product having a distribution peak at the DP2 oligomer and a higher average DP results which has improved surfactant and detergent properties.

The glycoside products of the reaction of an alcohol and saccharide may be represented by the formula $$ROG_x$$

wherein R is a residue of an alcohol, O is oxygen, G is a glycoside residue, and x is the average degree of polymerization (DP) resulting from weighting of the various mono-, di-, tri- and higher glycoside fractions present in the product and is a number of from about one to about three.

The average degree of polymerization is thus defined as the ratio of saccharide rings to the R groups in the alkyl glycoside. The monoglycoside fraction would have one saccharide ring, the diglycoside would have 2, the triglycoside would have 3 with the higher glycoside having corresponding more rings, the average of which in the currently available commercial product therefore being typically greater than about 1, generally in the order of about 1.2 to about 1.7, with preferred mixtures at about 1.3 to about 1.7.

The alkyl polyglycoside products represented by the formula above contain a lipophilic group, the R group, and a hydrophilic group, the $OG_x$ group. For detergent or surfactant-use application, the product should have a hydrophilic-lipophilic balance (HLB) of from about 10 to about 16, and preferably about 11 to about 14. The HLB value of a product may be calculated by the formula $$HLB = \frac{([MW_{AGU}] \times DP + MW_O)}{(([MW_{AGU}] \times DP + MW_O) + MW_R)} \times 100/5$$

where AGU is typically the anhydro glucose unit in G having a molecular weight of 162 and DP is the average degree of polymerization as predicted by Flory's statistical treatment. The present invention provides a method for the preparation of alkyl polyglycoside compositions having a desirable HLB for detergent or surfactant use application with the specific R groups of the alcohols employed in the reaction.

The lipophilic R groups in the alkyl polyglycosides are derived from alcohols, preferably monohydric, for the detergent, surfactant-use applications and should contain from about 8 to about 20, preferably about 9 to about 18 carbon atoms, with an average of about 10 to about 13 being most preferred, to provide R groups of sufficient length for detergent, surfactant-use applications, While the preferred R groups are saturated aliphatic or alkyl, there may be present some unsaturated aliphatic hydrocarbon groups. Thus, the preferred groups are derived from the fatty alcohols derived from the naturally-occurring fats and oils, such as octyl, decyl, dodecyl, tetradecyl, hexadecyl, octadecyl, oleyl and linoleyl, but R groups may be derived from synthetically produced Ziegler alcohols or oxo alcohols containing 9, 10, 11, 12, 13, 14 or 15 carbon atoms. The alcohols of naturally-occurring fatty acids typically contain an even number of carbon atoms and mixtures of alcohols are commercially available such as mixtures of $C_8$ and $C_{10}$, $C_{12}$ and $C_{14}$, and the like. Synthetically-produced alcohols, for example those produced by an oxo process contain both an odd and even number of carbon atoms such as the $C_9$, $C_{10}$, $C_{11}$ mixtures, which are also available commercially.

Saccharide reactants which can be employed to prepare the aforementioned glycoside surfactants include reducing monosaccharide materials containing 5 or 6 carbon atoms such as, for example, glucose, galactose, mannose, xylose, arabinose, fructose, etc. as well as materials which are hydrolyzable to form monosaccharides such as lower alkyl glycosides (e.g. methyl glycoside, ethyl glycoside, propyl glycoside, butyl glycoside, etc.), oligosaccharides (e.g. sucrose, maltose, maltotriose, lactose, zylobiose, melibiose, cellobiose, raffinose, stachyose, etc.) and other polysaccharides. Such saccharide reactants may be employed in dry (e.g. anhydrous) form or, if desired, may be employed in the form of hydrated solids or aqueous solutions thereof. If utilized in the form of a solution, it is preferred that the resulting reaction mixture contain only small amounts of water, i.e., less than about 1% by weight, preferably less than about 0.5% i.e. less than 0.25 or 0.1%.

While the preparation of the initial alkyl glycosides reaction mixture employed in the present invention forms no part of the present invention, a brief description generally of the preparation follows. The molar ratio of alcohol to monosaccharide in the reaction mixture can vary widely but is typically between about 1.5:1 to about 10:1, and preferably between about 2.0:1 to about 6.0:1. The particular molar ratio chosen depends upon the desired average degree of polymerization (DP) of the monosaccharide reacted with the alcohol. Preferably, the ratio of alcohol to monosaccharide will be chosen to allow the production of an alkyl glycoside product having a DP between about 1.2 to about 1.7, and more preferably about 1.3 and about 1.6.

The reaction between the hydrophobic alcohol reactant and the saccharide reactant to form the glycoside surfactant is typically conducted at an elevated temperature and in the presence of an acid catalyst. As a general rule, said reaction is preferably conducted at a temperature of from about 80° to about 140° C., preferably about 90° to about 120° C., and at pressures (about 10 to about 100 mm Hg absolute), which facilitate water removal, while at the same time maintaining the desired reaction temperatures.

Acid catalysts suitable for use include strong mineral acids such as hydrochloric acid, sulfuric acid, nitric acid, phosphoric acid, hypophosphorous acid, etc.; strong organic acids such as para toluenesulfonic acid, methanesulfonic acid, triflouromethanesulfonic acid, mono- or polyalkylated aryl mono- or polysulfonic acids such as dodecylbenzenesulfonic acid, etc.; and macroreticular acidic ion exchange resins such as macroreticular sulfonic acid ion exchange resins, perfluorinatedsulfonic acid resins, etc. Typically, said acid catalyst will be employed in an amount ranging from about 0.0005 to about 0.03 (preferably from about 0.002 to about 0.015) moles thereof per mole of saccharide used.

Typically, the above-described reaction process will be conducted over a reaction period of from about 1 to about 20 (preferably from about 2 to about 10) hours. Upon completion of the reaction, the acid catalyst is typically neutralized by an alkaline substance, preferably an alkali metal hydroxide such as sodium hydroxide, used in an amount about equal, on a stoichiometric basis, to the amount of material needed to neutralize the catalyst.

After neutralization of the acid catalyst, typically excess unreacted alcohol is removed. Alcohol removal is generally accomplished by evaporation, e.g. distillation, of the alcohol. The use of a wiped film evaporator is particularly convenient for this purpose, e.g. operated at about 160°-200° C. and about 0.1 to 3 mm Hg pressure. As indicated in the discussion of related art, other methods of removal of the alcohol may be employed including distillation techniques and supercritical extraction under conditions for removing alcohol to levels below about 5%, more desirably below about 2% by weight to about 0.5%.

At this point, the resulting commercial product, substantially devoid of alcohol, is typically a mixture of alkyl glycosides, in which for purposes of this invention the average alkyl group will contain from about 8 to about 20, preferably about 9 to about 18, most preferably an average of about 10 to about 13, carbon atoms, having the typical Flory distribution discussed earlier above.

In accordance with the present invention, the product is then treated under conditions which separate a highly concentrated monoglucoside stream from the mixture to provide a concentrated, purified alkyl monoglycoside and a polyglycoside product having improved detergent surfactant properties, containing the higher polyglycosides originally present in the mixture and a changed distribution or concentration of fractions due to the removal or separation therefrom of the monoglycoside. The changed distribution will vary dependent on the amount of monoglycoside separated from or removed from the original mixture.

A substantial portion of the monoglycoside will be removed or separated from the original reaction mixture. Preferably, at least about half of the monoglycoside content of the original reaction mixture will be separated therefrom. As indicated earlier, the typical Flory distribution of the reaction product after removal of the excess alcohol will have a monoglucoside content of about 50 to about 70% by weight. The polyglycoside content of the original reaction mixture will accordingly typically comprise about 50 to about 30% by weight. With removal of at least about half of the monoglycoside, the remaining mixture of alkyl polyglycosides and unremoved monoglycoside, will contain by weight at least about 45% of the polyglycosides having a DP of 2 and higher, and an average DP at least about 0.2 units higher than that of the original reaction mixture prior to removal of the monoglucoside. The remaining mixture will contain substantially all the polyglycosides present in the original reaction mixture prior to removal of the monoglycoside, particularly those having the higher DPs of DP4 and higher. Dependent on the particular specific method employed in separating the monoglycoside from the original reaction mixture, some small amounts of lower DP fractions, i.e. DP2 and DP3 fractions, may be removed along with the monoglucoside, particularly under conditions where large amounts of monoglucoside are removed from the reaction mixture. Preferably conditions are selected so that less than 10%, and more preferably less than 5%, of such polyglycoside fraction present in the original reaction mixture, will be removed along with the monoglycoside fraction removed. The monoglycoside fraction removed will accordingly be a concentrated, substantially pure product containing less than about 10%, more desirably less than about 5%, preferably less than 1% polyglycoside. By definition, a pure monoglycoside will have a degree of polymerization of 1 (DP1). With decreasingly smaller amounts of polyglycoside present, the concentrated, substantially pure alkyl monoglycoside product of this invention will accordingly approach a DP of 1, with the average DP being less than about 1.1, more desirably less than about 1.05 and preferably less than 1.02.

The separation of the monoglycoside from the original reaction mixture of alkyl monoglycoside and alkyl polyglycosides after removal of the alcohol, may be carried out by molecular distillation. Molecular distillation is a preferred method as it tends to be far more efficient and less expensive than other processes. Molecular distillation is accordingly preferred at the present time from a commercial operation viewpoint, and for purposes of this invention will be the method described in detail herein.

Figure 1:
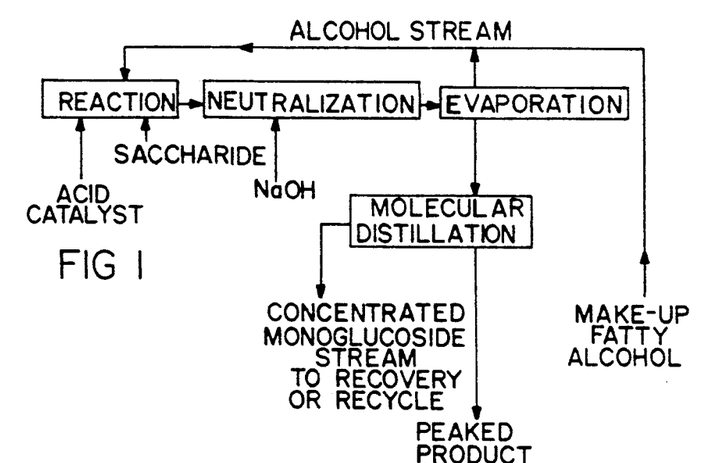
FIG. 1 is a block diagram of the process of preparation of the alkyl glycoside reaction product of an alcohol and a saccharide in the presence of an acid catalyst including the molecular distillation to provide the purified alkyl monoglycoside and improved detergency alkyl polyglycoside products of the present invention.

FIG. 1 of the drawing is a block diagram of a process of preparation of the alkyl glycoside reaction product of an alcohol and a saccharide in the presence of an acid catalyst, including an evaporation step and a molecular distillation step. As shown in FIG. 1, residual alcohol is removed and is typically recycled to the reactor.

Figure 3:
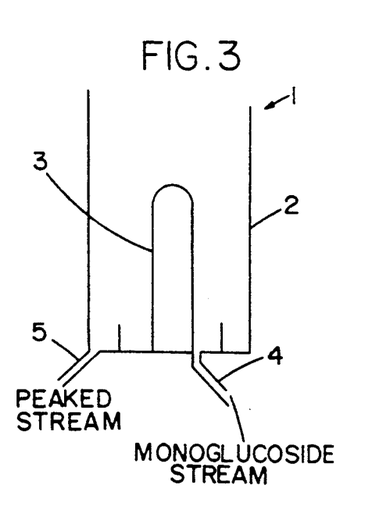
FIG. 3 is a diagram view of one molecular distillation still useful in the present invention with an internal condenser within the heated column.

FIG. 3 is a simplified, expanded, non-scale view of one molecular distillation still 1, useful in the present invention having an internal condenser 3, within the distillation heated chamber 2. The monoglcloside is withdrawn from the distillation chamber through passage 4, while the polyglycosides fractions now containing less monoglycoside is removed through conduit 5.

Referring again to FIG. 1, in the typical evaporation operation for removal of the excess alcohol, a temperature of about 170° to 200° C., preferably about 180° to about 200° C., is employed at pressures above 1 millibar. A molecular distillation as shown is operated at temperatures above 200° C., preferably above 230° and typically in the range of about 240° to about 250° C. By "molecular distillation" as used herein is meant short path, high vacuum distillation. On a laboratory scale, pressures of about 0.1 mbar and lower may be employed. On a commercial scale, pressures will desirably be in the range of 0.01 mbar and lower, preferably about 0.001 mbar or lower. In the molecular distillation, a very short distance is employed between the vaporization and condensing surfaces, which is as close as possible. In practice the actual gap is bounded by about 0.1 to about 10 times the mean free path of distilling molecules which is defined by kinetic theory. The residence time is as short as possible to minimize thermal degradation of the alkyl polyglycosides, less than about 2 minutes and preferably less than about 15 seconds.

Figure 4:
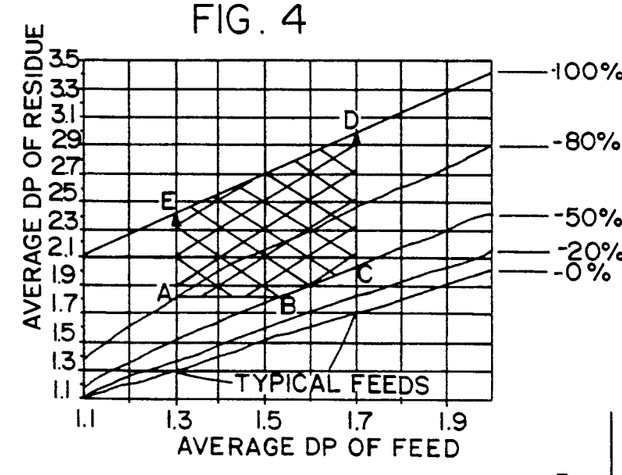
FIG. 4 is a graphical representation of the "peaked" versus the feed average DP at various percentages of initial monoglycosides removed and showing the preferred area ABCDE of the resulting alkyl polyglycoside products after use of the present invention from typical feeds having average DPs of about 1.3 and about 1.7.

As indicated earlier, the alkyl polyglycoside product after removal of monoglycoside will vary in its composition dependent on the amount of monoglycoside removed. In the molecular distillation process, if no polyglycoside is removed along with separation of the desired amount of monoglycoside, the resulting polyglycoside product will contain the polyglycosides present in the original mixture, along with any monoglycoside not separated from the original mixture. Thus, the relative distribution of the various components, mono- and poly-glycosides, in the resulting product changes, and the concentration in the product of the polyglycosides relative to the monoglycoside increases, as well as the concentration of individual polyglycosides to the total, i.e. DP2 and DP3 fractions in relation to the sum of all DP fractions. With the removal of monoglycoside the average DP of the resulting product is higher. FIG. 4 illustrates the average DP of preferred residue products of the present invention resulting from molecular distillation of typical feed having average DPs of about 1.3 to about 1.7. With removal of at least about 50% of the monoglucosides ($-50\%$ line), the preferred products of the present invention from such feeds will have an average DP of at least about 1.8 and about at least 0.2 units higher than the average DP of the initial feed and will fall within the trapezoidal area defined by ABCDE of FIG. 4. If the amount of monoglycoside separated from the original reaction mixtures is in a sufficient amount to provide that the monoglycoside retained in the resulting product is less than the total of DP2 and DP3 fractions, or more preferably, less than that of the DP2 fraction, it can be readily seen from FIGS. 2A and 2B illustrating Flory (solid bars) versus examples of "peaked" distributions (hatched bars), that the DP2 and DP3 distribution now illustrates a non-monoglycoside "peaked" distribution in the resulting products, which retain the DP4 and higher fractions in the resulting products prepared by molecular distillation.

The following examples serve to illustrate, but not limit, the invention. All parts and percentages are by weight, unless otherwise noted.

EXAMPLE 1

A crude reactor product from the reaction of a saccharide (glucose) and an alcohol (Lorol 1214A, an alcohol having a mixture of $C_{12}$, $C_{14}$ and $C_{16}$ alkyl groups in a weight ratio of 68, 26 and 6 respectively), in the presence of an acid catalyst was taken directly from a reactor. The reaction mixture at a concentration of about 26% dry solids (ds) was neutralized with 33 weight % sodium hydroxide using about 101% of theoretical amount of sodium hydroxide.

The neutralized reactor product was the concentrated to ca. 70% ds by vacuum distillation under "mild" conditions. This was accomplished in a Leybold Heraeus wiped film evaporator with external condenser at 2 mm Hg pressure, 105° C. feed temp., 160° C. evaporator body (wiped zone), 140° C. evaporator residue zone, 30°-35° C. external condenser temp., and a feed rate of ca. 600 cc/hr. The resulting product with Flory distribution was typically 65-75 ds, and flows at 80° C.

A "peaked" alkyl polyglycoside surfactant was prepared from this 70 ds product by high vacuum molecular distillation using a Leybold Heraeus wiped film molecular still with an internal condenser. Typical distillation conditions were: 0.01 millibar (ca. 8 microns, measured between the pump and cold trap), 110° C. feed temperature, 240° C. evaporator body (wiped zone), 200° C. residue zone, 140° C. internal condenser, and a feed rate of ca. cc/hr. The alkyl polyglycoside residue contained about 20 wt. % monoglucosides on an alkyl polyglycoside solids basis. To improve the color the recovered product was then bleached using hydrogen peroxide to provide a product typical having about 18-21 Klett color (5% solution at 4 cm length).

EXAMPLE 2

This example serves to illustrate the distribution of the various fractions in the product before and after distillation as described in Example 1. In this instance, about 79.7% of the monoglycoside (50% of the total initial weight) was removed changing the Flory distribution of the starting material to that indicated below in Table 1.

TABLE 1

|  | STARTING weight % | 79.7% MONOS REMOVED weight % |
|---|---|---|
| DP 1 | 62.7 | 25.4 |
| DP 2 | 21.2 | 42.4 |
| DP 3 | 8.7 | 17.4 |
| DP 4 | 3.9 | 7.7 |
| DP 5 | 1.8 | 3.6 |
| DP 6 | 0.9 | 1.7 |
| DP 7 | 0.4 | 0.8 |
| DP 8 | 0.2 | 0.4 |
| HIGHER | 0.2 | 0.4 |
| AVERAGE DP | 1.4 | 2.0 |

EXAMPLE 3

Distillations were conducted to effect separation of monoglycosides on $C_{11}$, $C_{12}$ and $C_{14}$ feeds. The conditions of the distillation and results can be seen from the following Table 2 which includes a sample of the $C_{12}$-$C_{14}$ product of Example 1.

TABLE 2

| Feed | DP Feed | Temperature °C. | Pressure mm | % DP 1 Removed | DP Residue |
|---|---|---|---|---|---|
| $C_{11}$ | 1.16 | 240 | 0.1 | 95 | 1.92 |
| $C_{12}$ | 1.39 | 242 | 0.1 | 80 | 1.97 |
| $C_{14}$ | 1.46 | 245 | .02 | 83 | 2.14 |
| $C_{12}$-$C_{14}$ (Example 1) | 1.38 | 240 | .008 | 83 | 2.01 |

As indicated initially above, the present invention results in a purified monoglycoside product stream which will find utility in applications where monoglycosides find utility or for conversion to other derivatives. It has also been discovered that the alkyl monoglucoside product removed as described above is useful as a starting feed material for preparing low mole ratios (e.g. 1.1 to 1.5 anhydroglucose groups per fatty group) alkyl polyglycoside products which may be prepared at high solids, above 40 weight/weight % in fatty alcohol. Thus, the alkyl monoglycosides isolated by molecular distillation, or the other methods described above, are mixed with the fatty alkyl (preferably $C_8$ and above) alcohol and heated in the presence of an acid catalyst, such as an alkylbenzene sulfonic acid to provide an alkyl polyglycoside with mole ratios of anhydroglucose to bound fatty groups of 1.5 or lower.

The acid catalysts are the same acid catalysts described earlier above in the preparation of the alkyl polyglycoside mixtures having the Flory distribution from which the monoglycoside forming the starting material herein has been removed. In a batch process the acid catalyst is employed in a level of about 1 to about 10 milliequivalents per mole of anhydroglucose, preferably at about 5 to about 8 milliequivalents. Similarly, the fatty alcohols are the same as noted earlier containing about 8 to about 20, preferably 9 to about 18, and most preferably about 10 to about 13, carbon atoms. The alcohol is employed in an amount to provide less than about 4 moles of alkyl groups per anhydroglucose unit, preferably about 1.5 to about 3 moles alkyl group per anhydroglucose unit. The temperature and pressures employed are also the same, about 90° to about 120° C. being preferred at pressures of about 10 to about 100 mm Hg absolute). Typically, about 100° C. is employed.

The polymerization reaction may be carried out in a batch or continuous process. In a continuous process, a monoglucoside fraction resulting from molecular distillation of an alkyl polyglycoside/fatty alcohol feed is continuously injected or fed with catalyst or alcohol/catalyst mixtures and passed through a heated zone. The residence time in the heated zone and the catalyst level are adjusted to give the desired product. In a desirable application of the present invention, the monoglucosides are continuously distilled and isolated together with the fatty alcohol, mixed with catalyst, and passed through a heated zone characterized by high temperatures and short residence time with sufficient vacuum to remove any water formed in the process. A wiped film evaporator is an example of a suitable piece of equipment for the reaction zone.

EXAMPLE 4

The use of the alkyl monoglycoside stream removed from the Flory distribution by molecular distillation, as described above, is illustrated by the following, in which a $C_{12}$ alkyl monoglycoside fraction and a $C_{12}$ alkanol were employed with 6 milliequivalents of LAS catalyst and 2.25 moles of fatty alkyl groups per anhydroglucose unit at about 60% dry solids by weight, at a temperature of 100° C. The results may be seen from Table 3 below:

TABLE 3

| COMPONENT | 0 Min | 60 Min | 120 Min | 180 Min |
|---|---|---|---|---|
| % FOH | 43.32% | 45.78% | 46.28% | 48.17% |
| % MONOSACCAHARIDES | 1.17% | 1.05% | 1.11% | 0.87% |
| % DP1* | 99.0% | 77.0% | 69.8% | 66.3% |

TABLE 3-continued

| COMPONENT | 0 Min | 60 Min | 120 Min | 180 Min |
|---|---|---|---|---|
| FLORY DP | 1.01 | 1.20 | 1.29 | 1.34 |

Compositions determined by TMS/GC with internal standard
*Alkyl glycoside basis

The alkyl polyglycoside remaining after removal of monoglycoside by molecular distillation, or the other processes described, will result in a lower viscosity product where the products have less than about 40%, preferably less than about 35% by weight monoglycoside and an average DP of about 1.8 and above up to about 3.0, preferably about 1.8 to about 2.5. The preferred products will further contain less than 20% by weight of polyglycoside having a DP of 5 and higher. Such products retain the improved surface-active properties of the polyglycoside product resulting from the present invention, but the products afford lower solution viscosity and are then easier to handle and may be shipped with less water or cosolvent. This unexpected advantage also results in lower handling losses and provides for greater flexibility in formulating finished blended surfactant products in the various end-use applications in which the alkylpolyglycosides find utility, such as cleaning compositions, soaps, detergents, shampoos, personal care products and cosmetics. The products, accordingly, avoid the problems encountered in high viscosity solutions which are difficult to pump, blend and dilute and frequently result in loss of material due to difficulty in completely emptying storage vessels of product too viscous to flow readily. While cosolvents such as alcohols may be used to dilute highly viscous products, such dilution with alcohols and/or water result in higher shipping costs per pound of active product. Further alcohols or other cosolvents may result in adverse flammability characteristics and their presence may cause difficulty in formulating a finished product blend in which such cosolvents are undesirable. The products of the present invention overcome such problems. The foregoing can be demonstrated by the following Example 5.

EXAMPLE 5

In this example, the Brookfield viscosity in centipoise (cps) at 25° C. was measured of 10% solids solution in water of polyglycosides from $C_{12}$ and $C_{14}$ alcohols containing varying amounts of monoglycoside (DP1). The results can be seen from the following Table 4.

TABLE 4

| Alkyl Group | % DP1 (by weight) | Viscosity (cps) |
|---|---|---|
| $C_{12}$ | 60.1 | 810 |
| $C_{12}$ | 48.1 | 157 |
| $C_{12}$ | 37.6 | 8 |
| $C_{14}$ | 48.9 | 30,750 |
| $C_{14}$ | 37.6 | 1,213 |
| $C_{14}$ | 29.8 | 9 |

It can be seen from the foregoing that low viscosities below are achieved with the longer chain ($C_{14}$) alkyl polyglycoside at monoglycoside content below 35%, about 30%. With the shorter chain ($C_{12}$) alkylpolyglycoside, the low viscosity, below 10 cps. is achieved at a level below about 40%.

In order to achieve these low viscosities, the monoglycoside content should be below 40%, preferably below about 35%, the average DP should be above 1.8, and well less than about 20% of polyglycosides of DP5 and higher.

As indicated earlier, the removal of the monoglycoside from an essentially Flory distribution of monoglycoside and polyglycoside provides a polyglycoside having enhanced surfactant properties. When about half of the monoglycoside is separated from a Flory distribution reaction product, the polyglycoside having DPs of 2 and 3, originally present, are retained and accordingly present in the resulting polyglycoside product remaining. If the monoglycoside content of the initial Flory distribution is typically on the order of about 50–70% by weight as noted earlier, the remaining polyglycoside product will accordingly after removal of the monoglycoside by molecular distillation, or other method, contain about 25–35% diglycoside and the average DP of the resulting composition above about 1.8 to about 2.8. The resulting product will have an HLB in the range of about 10 to about 18, preferably about 12 to about 16, the HLB range which is most desirable for surfactant application.

In an alkyl polyglycoside product resulting from the reaction of an acid alkanol and a saccharide in the presence of an acid catalyst, as described earlier contain various fractions of degrees of polymerization. The presence of polar glycoside fractions in the product, which may be designated as those having a DP of 5 and higher, have been found to have low laundry cleaning or surfactant activity, such fraction having HLB values of about 16 and higher. The presence of such polar fractions, however, were found not to reduce the cleaning action or surfactant activity of the DP2, DP3 and DP4 fraction present now in higher or maximized levels in the polyglycoside product remaining after removal of the monoglycoside, particularly after removal of half or more of the monoglycoside. As indicated, the level in the product of these polar fractions are preferably maintained at less than about 20%, and preferably less than about 10 or 15%. With the removal of the monoglycoside as described in the present invention, these polar fractions will also be more concentrated in the resulting polyglycoside. With a typical Flory distribution described earlier, removal of the monoglycoside to the extent of only about 10% monoglycoside is retained in the resulting polyglycoside, the polar fractions will be below the levels noted above. Small amounts of monoglycosides in the resulting polyglycoside were found not to be deleterious to the surfactant or detergent activity of the product. As the amounts of monoglycoside increase to above about 25%, the surfactant performance of the product tends to be affected due to surface properties of the monoglycoside itself and its effect on lowering the overall average DP to the lower level of about By use of the present invention, the isomer distribution in the alkyl polyglycoside product may be controlled or adjusted to provide improved surfactant or detergency properties to the extent that the product may function as a stand-alone surfactant, tending to match the performance of Neodol 25-7 (an ethoxylated [7EO] alcohol having mixed $C_{12}$ to $C_{15}$ alkyl groups), typically considered a standard for stand-alone properties, against which other products are compared, particularly in laundry cleaning application on dust/sebum soiled cloth using cotton and polyester/cotton (Dacron/cotton) cloth. The results of laundry cleaning action of a "peaked" product (a peak of DP2 or DP 2 plus DP 3) compared to Neodol 25-7 can be seen from the following example.

EXAMPLE 6

Pure alcohol cuts of alkyl polyglycoside surfactants were prepared (a $C_{11}$, $C_{12}$ and $C_{14}$), the peaked residues described in Example 3. The samples were then tested and evaluated for Draves Wetting Time, Ross Miles Foam Height and Laundry Detergency. The test conditions were as follows:

Draves Wetting Time—run at room temperature (77° F.) using 0.1 wt. % surfactant solution. Wetting times were also run at varying concentrations to obtain a 20-second wetting time.

Ross Miles Foam Height-modified—run at room temperature (77° F.) using 0.1 wt. % surfactant solution.

Laundry Detergency Testing—used 1 liter of 150 ppm (Ca:Mg, 3:2) containing TEA (buffer) at a temperature of 100° F. The soil cloth was (Scientific Services) Dust Sebum Cotton and Dacron/Cotton. The total cleaning units is the reflectance of soiled cloth after washing minus reflectance of soiled cloth before washing. A difference of three cleaning units is needed to say there is a difference in cleaning action between products.

The results of the Draves Wetting Time and Ross Miles Foam Height can be seen from the following Table 5A:

TABLE 5A

| Alkyl Polyglycoside Surfactant | 77° F. Draves Wetting | Foam (mm) 77° F. | |
|---|---|---|---|
| | | 0 min. | 5 min. |
| Regular $C_{11}$ | 260 sec | 120 | 120 |
| Peaked $C_{11}$ | 47 sec | 155 | 155 |
| Regular $C_{12}$ | 20 sec | 103 | 103 |
| Peaked $C_{12}$ | 42 sec | 156 | 156 |
| Regular $C_{14}$ | 92 sec | 40 | 40 |
| Peaked $C_{14}$ 1 | 70 sec | 98 | 98 |
| Peaked $C_{14}$ 2 | 315 sec | 80 | 80 |

1 Contains approximately 25% DP1 Glycoside
2 Contains approximately 10% DP1 Glycoside Table 5B, below, illustrates the amount of surfactant needed to get a 20-second wetting time for the $C_{11}$ and $C_{12}$ regular (R) and peaked (P) products:

TABLE 5B

| Time (Seconds) | % Surfactant Solution | | | |
|---|---|---|---|---|
| | $C_{11}$(R) | $C_{11}$(P) | $C_{12}$(R) | $C_{12}$(P) |
| 20 | 0.21 | 0.23 | 0.10 | 0.24 |

The improvement in laundry detergency of the peaked product compared to the original alkyl polyglycoside surfactant can be seen from the following Table 5C. In all cases the peaked products have more cleaning ability than the original regular product, and approach the Neodol 25-7, a linear alcohol ethoxylate, shown in the Table.

TABLE 5C

| g/l Surfactants | Cleaning Units | | | | | | |
|---|---|---|---|---|---|---|---|
| | $C_{11}$(R) | $C_{11}$(P) | $C_{12}$(R) | $C_{12}$(P) | $C_{14}$(R) | $C_{14}$(P) | Neodol |
| .12 | 4.6 | 8.1 | 16.4 | 21.2 | 16.6 | 20.8 | 24.2 |
| .24 | 5.3 | 20.2 | 22.3 | 24.2 | 19.9 | 22.6 | 29.8 |
| .36 | 7.7 | 24.6 | 24.3 | 25.2 | — | — | 29.6 |

In end-use formulations, the alkyl polyglycosides resulting from the present invention, the polyglycoside will typically be present in amount from ½ to about 80% and more typically about 30, 50 or 70% in an aqueous solution form. A granule form of the alkyl polyglycoside may be prepared by spray drying an aqueous solution of the polyglycoside and adjuvants to provide a substantially dry, non-sticky granule. In such a product, the alkyl polyglocoside may comprise up to about 98-99% of the granule with very little water or other solvent, along with any optional adjuvants. The composition will utilize other compatible ingredients, which will vary dependent on the specific end-use application desired, the various end-use application having been discussed earlier referring to many patents. Thus, the compositions may contain other surfactants, detergency builders, soil-suspending agents, brightening agents, abrasives, dyes, fabric-conditioning agents, hair conditioning agents, hydrotropes, solvents, fillers, etc. Such materials assist the alkyl polyglycoside in its end-use application, and are, accordingly, auxiliary, optimal, reagents referred to herein as "adjuvants." Formulations for various end-use applications, accordingly, may generally comprise:

(a) Alkyl polyglycoside surfactant of the present invention in an amount of about 0.5 to 99% by weight, (b) Solvent (water or other non-aqueous liquid or mixtures thereof), in an amount of about 0.5 to about 99.5% by weight and (c) Adjuvant (optional ingredient based on particular end-use application) in an amount up to about 99.5% by weight.

Typical illustrative formulations for various end-use applications are as follows:

| Ingredient | Wt % |
|---|---|
| 1. HEAVY DUTY - ALL PURPOSE HARD SURFACE CLEANER | |
| Water | 80 |
| Tetrapotassium pyrophosphate | 5 |
| Sodium metasilicate pentahydrate | 3 |
| Sodium hydroxide (50%) | 2 |
| Sodium xylene sulfonate (40%) | 5 |
| Alkyl polyglycoside (50%) | 5 |
| 2. ALUMINUM CLEANER - ALKALI | |
| Water | 58 |
| Sodium EDTA | 2 |
| Sodium gluconate | 2 |
| Sodium silicate (SiO$_2$/Na$_2$O = 2.5) | 20 |
| Potassium hydroxide (45%) | 15 |
| Alkyl polyglycoside (50%) | 3 |
| 3. LAUNDRY DETERGENT | |
| (a) Alkyl polyglycoside (50%) | 30 |
| Water | 30 |
| Sodium lauryl sulfate (28%) | 35 |
| Sodium citrate | 5 |
| Optional - brightners, color, fragrance | QS* |
| (b) Alkyl polyglycoside (50%) | 32 |
| Water | 50 |
| Sodium laureth sulfate (25%) | 8 |
| Ethoxylated fatty alcohol | 10 |
| Optional - brighteners, color, | QS* |
| 4. LIQUID HAND SOAP | |
| Alkyl polyglycoside (50%) | 16.0 |
| Water | 62.5 |
| Sodium laureth sulfate (25%) | 16.0 |
| Alkanolamide | 4.0 |
| Lanolin | .5 |
| Etylene glycol mono-stearate | 1.0 |
| Color, fragrance, preservative | QS* |
| 5. HAIR SHAMPOO | |
| Alkyl polyglycoside (50%) | 6 |
| Water | 61 |

| Ingredient | Wt % |
|---|---|
| —continued | |
| Sodium laureth sulfate (25%) | 30 |
| NaCl | 3 |
| Color, fragrance, preservative | QS* |
| The following illustrates a typical liquid dish detergent employing an alkyl monoglycoside component (minimum of 90% monos) employed in combination with a nonglycoside surfactant. | |
| 6. LIQUID DISH DETERGENT | |
| Alkyl monoglycoside (50%) | 18 |
| Water | 59 |
| Sodium dodecylbenzene sulfonate (60%) | 20 |
| Alkanolamide | 3 |
| Color, fragrance, preservative | QS* |

*Quantity sufficient

What is claimed is:

1. A method of producing an alkyl polyglycoside composition having enhanced surfactant properties and a purified alkyl monoglycoside composition, in which the alkyl group contains from about 8 to about 20 carbon atoms comprising (a) providing a reaction mixture of alkyl monoglycoside and alkyl polyglycoside having an essentially Flory distribution resulting from the reaction of an alkyl alcohol and a saccharide in the presence of an acid catalyst;

(b) molecularly distilling said reaction mixture under conditions so as to separate monoglycoside from the polyglycoside; and (c) recovering from the molecular distillation (i) a highly concentrated, purified alkyl monoglycoside stream essentially free from polyglycoside and (ii) an alkyl polyglycoside composition containing polyglycosides having DPs of 2 and higher originally present in said reaction mixture and having an HLB in the range of about 10 to about 16 and an average DP at least about 1.8 and at least about 0.2 units higher than the average DP of the reaction mixture before separation of the alkyl monoglycoside.

2. A method as defined in claim 1, wherein said highly concentrated, purified alkyl monoglycoside has an average DP less than about 1.1.

3. A method as defined in claim 1, wherein said alkyl polyglycoside composition after separation of monoglycoside from the reaction mixture has an average DP of about 1.8 to about 3.

4. A method as defined in claim wherein the amount by weight of monoglycoside separated from the reaction mixture is at least half the amount of monoglycoside present in the original reaction mixture.

5. A method as defined in claim 4, wherein said original reaction mixture before the molecular distillation has an average DP of about 1.3 to about 1.7 and said alkyl polyglycoside composition recovered after the molecular distillation has an average DP within the trapezoidal area ABCDE of FIG. 4.

6. A method as defined in claim 4, wherein the amount of monoglycoside present in the alkyl polyglycoside composition after separation of monoglycoside therefrom is less than about 30% by weight.

7. A method as defined in claim 4, wherein the amount of the monoglycoside present in the alkyl polyglycoside composition after separation of monoglycoside therefrom is less than about 20% by weight.

8. A method as defined in claim 1 wherein said alkyl monoglycoside is removed by molecularly distilling said alkyl glycoside reaction mixture having a Flory distribution at a temperature above about 200° C. and a pressure of about 0.1 mbar and lower for a time sufficient to remove the alkyl monoglycoside in an amount to provide a polyglycoside residue with an average DP of at least 1.8.

9. A method as defined in claim 8 wherein the vaporizing and condensing surfaces in said molecular distillation is in the range of about 0.1 to about 10 times the mean free path of distilling molecules.

10. A method as defined in claim 8 in which said distillation temperature is in the range of about 220° to 260° C.

11. A method as defined in claim 10 wherein said distillation temperature is about 240° to about 250° C.

12. A method as defined in claim 8 wherein at least about half of the alkyl monoglycoside in said alkyl glycoside reaction mixture having a Flory distribution is removed providing a retained polyglycoside composition having a monoglycoside content less than about 30% by weight based on the total retained polyglycoside residue composition.

13. A method as defined in claim 12 wherein said monoglycoside content in said retained polyglycoside composition is less than about 25% by weight.

14. A method of producing an alkyl polyglycoside composition having enhanced surfactant properties and a purified alkyl monoglycoside composition, in which the alkyl group contains from about 8 to about 20 carbon atoms comprising
  (a) providing a reaction mixture of alkyl monoglycoside and alkyl polyglycoside having an essentially Flory distribution resulting from the reaction of an alkyl alcohol and a saccharide in the presence of an acid catalyst;
  (b) molecularly distilling said reaction mixture at a pressure of 0.1 mbar or lower and a temperature above 200° C. so as to separate at least about half of the monoglycoside from the polyglycoside; and
  (c) recovering from the molecular distillation
    (i) a highly concentrated, purified alkyl monoglycoside stream essentially free from polyglycoside and
    (ii) an alkyl polyglycoside composition containing polyglycosides having DPs of 2 and higher and having an HLB in the range of about 10 to about 16 and an average DP at least about 1.8 and at least about 0.2 units higher than the average DP of the reaction mixture before separation of the alkyl monoglycoside.

15. A method as defined in claim 14 wherein the distillation temperature is in the range of about 220° to about 260° C.

16. A pressure as defined in claim 15 wherein said temperature is in the range of about 240° to about 250° C.

17. A method as defined in claim 15 wherein said original reaction mixture before the molecular distillation has an average DP of about 1.3 to about 1.7 and said alkyl polyglycoside composition recovered after the molecular distillation has an average DP within the trapezoidal area ABCDE of FIG. 4.

18. The retained alkyl polyglycoside composition of the process of claim 1.

19. The alkyl polyglycoside residue after the molecular distillation process defined in claim 14.

20. The alkyl polyglycoside residue after the molecular distillation process defined in claim 17.

21. An alkyl polyglycoside composition having increased surfactant properties and an HLB in the range of about 10 to about 16 and having a non-Flory distribution of glycosides, comprising a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3.

22. An alkyl polyglycoside composition as defined in claim 21 in which the alkyl monoglycoside content is less than about 30% by weight.

23. An alkyl polyglycoside composition as defined in claim 22 in which the amount of alkyl monoglycoside is less than about 25% by weight.

24. An alkyl polyglycoside composition as defined in claim 21 in which the amount of polyglycoside having a degree of polymerization above 4 is less than about 20% by weight.

25. An alkyl polyglycoside composition as defined in claim 21 in which the alkyl group contains from about 8 to about 18 carbon atoms.

26. An alkyl polyglycoside composition as defined in claim 25 in which the average carbon chain length of the alkyl group is from about 9 to about 13.

27. An alkyl polyglycoside composition as defined in claim 21 and falling within the trapezoid area ABCDE of FIG. 4.

28. An alkyl polyglycoside composition as defined in claim 27 derived from the removal of at least about half of the alkyl monoglycoside from a mixture of alkyl monoglycoside and alkyl polyglycoside having a Flory distribution and an average DP of about 1.3 to about 1.7.

29. A method of preparing an alkyl polyglycoside with mole ratios of anhydroglucose to bound alkyl groups of 1.5 or lower in which the alkyl group contains from about 6 to about 20 carbon atoms comprising reacting an alkyl monoglycoside fraction essentially free of polyglycoside with an alkyl alcohol in which the alkyl group contains from about 6 to about 20 carbon atoms in the presence of an acid catalyst for a time sufficient to provide an alkyl polyglycoside having a mole ratio of anhydroglucose to alkyl group of about 1.1 to about 1.5.

30. A process as defined in claim 29 wherein said alkyl monoglycoside is the monoglycoside fraction (a) of claim 1.

31. A process as defined in claim 29, wherein the alkyl group in said monoglycoside contains from about 8 to about 16 carbon atoms.

32. A process as defined in claim 31 wherein said alkyl alcohol is employed at a level to provide less than about 4 moles alkyl group to anhydroglucose unit.

33. A process as defined in claim 32 wherein said alcohol is employed at a level to provide about 1.5 to about 3 moles alkyl group per anhydroglucose unit.

34. A process as defined in claim 32 wherein said acid catalyst is present in an amount of about to about 10 milliequivalents per mole of anhydroglucose.

35. A process as defined in claim 34 wherein said catalyst is present in an amount of about 5 to about 8 milliequivalents per mole of anhydroglucose.

36. A process as defined in claim 29 wherein said monoglycoside and said alcohol is heated at a temperature of about 80° to about 140° C.

37. A process as defined in claim 36 wherein said acid catalyst is an alkyl benzene sulfonic acid in which the alkyl group contains from about 8 to about 20 carbon atoms.

38. An alkylpolyglycoside having a mole ratio of anhydroglucose to bound alkyl groups of about 1.5 or lower prepared by the process of claim 29.

39. An alkyl polyglycoside as defined in claim 38 having a mole ratio of anhydroglucose to bound alkyl group of about 1.1 to about 1.5.

40. A surfactant composition comprising from about 0.5 to about 99% by weight of the alkyl polyglycoside composition defined in claim 21.

41. A surfactant composition as defined in claim 40 and further comprising a solvent and an adjuvant.

42. A surfactant as defined in claim 41 wherein said solvent is present in an amount of about 0.5 to about 99.5% by weight and said adjuvant is present in an amount up to about 99.5% by weight.

43. A hard surface cleaner containing the surfactant composition of claim 40.

44. A laundry detergent containing the surfactant composition of claim 40.

45. A liquid hand soap containing the surfactant composition of claim 40.

46. A hair shampoo containing the surfactant composition of claim 40.

* * * * *